(12) United States Patent
Cesarczyk

(10) Patent No.: US 6,926,678 B1
(45) Date of Patent: *Aug. 9, 2005

(54) SAMPLE COLLECTION AND DELIVERY DEVICE

(75) Inventor: Edward J. Cesarczyk, North Easton, MA (US)

(73) Assignee: Avitar, Inc., Canton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/712,682

(22) Filed: Sep. 27, 1996

(51) Int. Cl.⁷ .............................. A61B 5/00; A61B 10/00
(52) U.S. Cl. ...................................... 600/573; 600/572
(58) Field of Search .............................. 600/573, 574, 600/576, 579, 582, 569, 572, 362, 575; 604/1, 604/2, 3, 11–18; 422/58, 56, 61, 100; 435/294.1, 435/295.1; 401/198, 199, 96; 15/244.1, 244.3, 15/224.4, 159.1, 160; 132/317, 318, 320; 433/80

(56) References Cited

U.S. PATENT DOCUMENTS

| | | | | |
|---|---|---|---|---|
| 86,453 A | * | 2/1869 | Robinson, Jr. et al. ...... | 401/131 |
| 489,152 A | * | 1/1893 | Legg ........................... | 15/118 |
| 668,285 A | * | 2/1901 | Dayton ....................... | 15/244.1 |
| 1,313,566 A | * | 8/1919 | Trowbridge ................. | 141/24 |
| 1,687,472 A | * | 10/1928 | Dorman et al. .............. | 604/1 |
| 1,903,664 A | | 4/1933 | Yutts | |
| 2,249,912 A | * | 7/1941 | Oxley ......................... | 15/118 |
| 2,355,917 A | * | 8/1944 | Knight ........................ | 604/11 |
| 2,712,143 A | * | 7/1955 | Palma, Jr. et al. .......... | 15/119.2 |
| 2,847,000 A | * | 8/1958 | Nieburgs ..................... | 604/16 |
| RE24,666 E | * | 7/1959 | Draghi ........................ | 600/572 |
| 2,902,041 A | * | 9/1959 | Bau ............................. | 132/318 |
| 3,056,998 A | * | 10/1962 | Ebner .......................... | 134/901 |
| 3,152,352 A | * | 10/1964 | Kosik, Jr. ................... | 401/132 |
| 3,457,014 A | * | 7/1969 | Ward .......................... | 401/183 |
| 3,491,397 A | * | 1/1970 | Hesener ...................... | 15/118 |
| 3,783,469 A | * | 1/1974 | Siemund ..................... | 15/244.1 |
| 3,831,598 A | * | 8/1974 | Tice ............................ | 128/172.1 |
| 3,871,375 A | * | 3/1975 | Nennett ....................... | 604/1 |
| 3,946,457 A | * | 3/1976 | Robinson .................... | 15/119.1 |
| 4,079,936 A | * | 3/1978 | Schachter ................... | 463/47.2 |
| 4,123,224 A | | 10/1978 | Givner et al. ............... | 422/59 |
| 4,157,709 A | * | 6/1979 | Schuster et al. ............ | 604/14 |
| 4,283,809 A | * | 8/1981 | Prost .......................... | 15/145 |
| 4,332,251 A | * | 6/1982 | Thompson .................. | 604/16 |
| 4,778,457 A | * | 10/1988 | York ........................... | 604/290 |
| 4,820,259 A | * | 4/1989 | Stevens ....................... | 604/2 |
| 4,828,419 A | * | 5/1989 | Porter et al. ................ | 132/317 |
| 4,846,802 A | * | 7/1989 | Sanders, III ................ | 604/15 |
| 4,925,327 A | * | 5/1990 | Wirt ............................ | 401/205 |
| 4,935,001 A | * | 6/1990 | George ........................ | 604/1 |
| 5,000,193 A | | 3/1991 | Heelis et al. ............... | 128/760 |
| 5,000,202 A | * | 3/1991 | Stepan ........................ | 604/1 |
| 5,022,409 A | | 6/1991 | Goldstein et al. .......... | 128/760 |

(Continued)

Primary Examiner—Gregory L. Huson
Assistant Examiner—Fenn C. Mathew
(74) Attorney, Agent, or Firm—George W. Neuner; Edwards & Angell LLP

(57) ABSTRACT

A specimen collecting device is disclosed. The device has an elongated foam member that is circumscribed by a hollow tubular member along a portion of its longitudinal axis. The hollow tubular member has a cross sectional area less than the uncompressed cross sectional area of the foam member so that the foam member is compressed along the circumscribed portion.

10 Claims, 1 Drawing Sheet

U.S. PATENT DOCUMENTS

| | | | |
|---|---|---|---|
| 5,147,288 A * | 9/1992 | Schiavo | 604/1 |
| 5,250,412 A * | 10/1993 | Giegel | 435/287.2 |
| 5,260,031 A | 11/1993 | Seymour | 422/101 |
| 5,268,148 A * | 12/1993 | Seymour | 422/101 |
| 5,283,038 A | 2/1994 | Seymour | 422/101 |
| 5,339,829 A | 8/1994 | Thieme et al. | 128/760 |
| 5,376,337 A * | 12/1994 | Seymour | 422/101 |
| 5,380,492 A | 1/1995 | Seymour | 422/101 |
| 5,393,496 A | 2/1995 | Seymour | 422/101 |
| 5,479,937 A | 1/1996 | Thieme et al. | 128/760 |
| 5,490,736 A * | 2/1996 | Haber et al. | 401/132 |
| 5,494,646 A | 2/1996 | Seymour | 422/101 |
| 5,531,671 A * | 7/1996 | Bennett | 604/1 |
| 5,591,507 A * | 1/1997 | Jones | 15/114 |
| 5,611,687 A * | 3/1997 | Wagner | 401/198 |
| 5,675,858 A * | 10/1997 | Von Meyer | 15/260 |
| 5,704,906 A * | 1/1998 | Fox | 604/1 |
| 5,816,270 A * | 10/1998 | Nadel | 132/320 |
| 6,200,275 B1 * | 3/2001 | Cesarczyk | 600/573 |

* cited by examiner

SAMPLE COLLECTION AND DELIVERY DEVICE

FIELD OF THE INVENTION

The present invention is related to devices for collection of specimen and delivery of specimen for diagnostic testing, particularly collecting and delivering saliva for diagnostic tests. The device of the present invention is particularly useful for collecting and delivering a specimen to a sample collection matrix from which a DNA template for PCR can be isolated.

BACKGROUND OF THE INVENTION

Various methods and devices have been used to collect and deliver specimen for diagnostic testing. One conventional method for collecting a saliva specimen is to use a cotton swab. The saliva sample can then be applied to a test device by contact with the swab or the sample can be rinsed from the swab.

Various devices comprising test tube like structures with sample absorbing means have been described for collecting biological samples for diagnostic testing. Examples of such devices are described in U.S. Pat. No. 4,123,224, U.S. Pat. No. 5,000,193, U.S. Pat. No. 5,022,409, U.S. Pat. No. 5,260,031, U.S. Pat. No. 5,268,148, U.S. Pat. No. 5,283,038, U.S. Pat. No. 5,339,829, U.S. Pat. No. 5,376,337, U.S. Pat. No. 5,380,492, U.S. Pat. No. 5,393,496, U.S. Pat. No. 5,479,937 and U.S. Pat. No. 5,494,646.

SUMMARY OF THE INVENTION

The present invention provides a simple device for collecting and delivering a specimen for diagnostic testing. In accord with the present invention, a specimen collecting device comprises an elongated foam member having a longitudinal axis and an uncompressed cross sectional area, the elongated foam member being circumscribed by a hollow tubular member along a portion of the longitudinal axis, the hollow tubular member has a cross sectional area less than the uncompressed cross sectional area of the foam member so that the foam member is compressed along the circumscribed portion.

The sample collection device of the present invention is particularly useful for collecting saliva specimen and delivering the sample to a DNA collection matrix from which DNA for PCR testing can be isolated. The collection device of the present invention provides a simple and inexpensive method for collecting and delivering the saliva sample. Further, in preferred embodiments, the foam member of the collection device provides more consistent and accurate samples.

The invention also provides a method for obtaining a DNA template for PCR. The method comprises: providing a sample collection device as described above; inserting one end of the sample collecting device into a patient's mouth to absorb saliva into the foam member; delivering a sample of the saliva to a collection matrix by contacting the end of the sample collecting device with the collection matrix; drying the sample on the collection matrix; and subsequently isolating DNA from the sample for PCR.

The sample collection devices of the present invention can be used to provide saliva samples for DNA testing for forensic and paternal identification, RNA testing, antibody testing, testing for particular drugs, and other similar diagnostic procedures.

DETAILED DESCRIPTION OF THE INVENTION INCLUDING PREFERRED EMBODIMENTS

Figure 1:
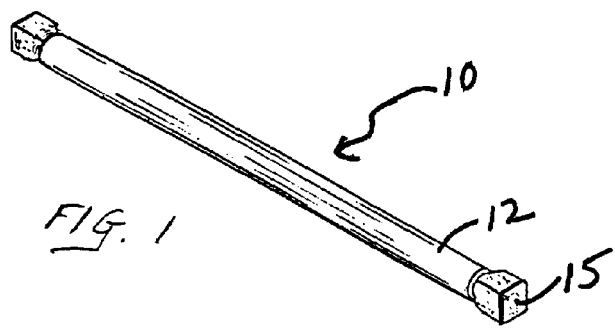
FIG. 1 is an isometric view of a sample collection device in accord with one embodiment of the present invention.
Figure 2:
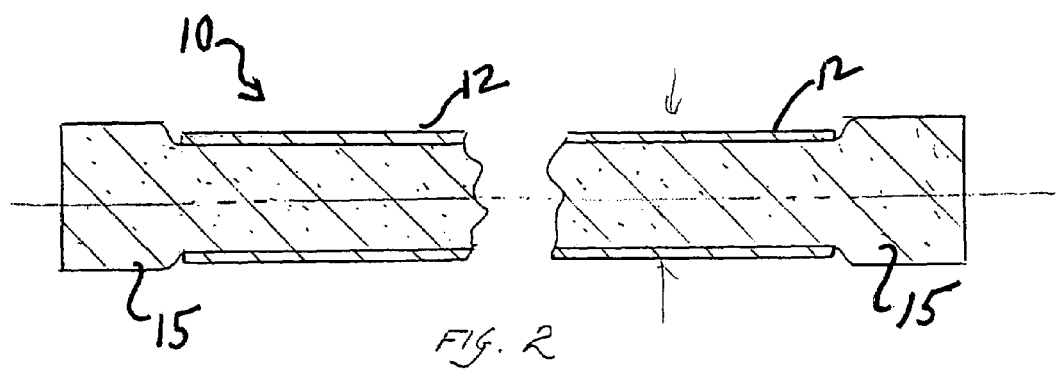
FIG. 2 is a cross sectional view along the longitudinal axis of the sample collection device of FIG. 1.

The sample collection device in accord with the present invention will be described with reference to the drawings. FIGS. 1 and 2 illustrates an embodiment of the present invention wherein a sample collection device 10 is made with a hollow tube member 12 containing an elongated piece of foam 15. The foam member 15 is compressed along its longitudinal axis where it is circumscribed by the tube 12. At the end of the sample collection device 10, the foam member 15 protrudes from the tube 12. The protruding volume of foam is the primary location for absorption of the sample for delivery for testing. Generally, the foam will protrude from the end of the tube a distance equal to about 25% to about 125% of the mean diameter of tube. If the tube is not circular, the largest dimension of the cross section can be used to approximate the mean diameter for this purpose. Alternatively, the foam will protrude generally a distance of about 0.125 inch to about 0.625 inch from the end of the tube, depending upon the diameter of the tube. Preferably, the foam protrudes from the tube a distance equal to the mean diameter of its uncompressed cross section. As illustrated, the foam member preferably protrudes from both ends of the tube. However, protrusion from only one end is required for convenient collection of a specimen. In some applications, protrusion of the foam member from only one end may be desirable.

The foam member 15 can be made of a variety of absorbent foams. Preferably, the foam is formed and cut to the desired size to expose the cell structure rather than a molded foam part having a surface skin. Preferred materials for the foam member include, for example, polyurethane foam, polyethylene foam, polyvinylchloride foam, ethylvinylacetate foam, polyethylene/ethylvinylacetate foam, polyester foam and polyether foam. Absorbent Porex™, silicone and latex foams can also be used. A particularly useful foam for the collection of saliva is a polyurethane foam sold under the mark HYDRASORB® by Avitar, Inc., Canton, Mass.

The preferred polyurethane foam has a uniform cell count of about 60 or more cells per linear inch. More preferably, the uniform cell count is about 80 to 120 cells per linear inch.

The tube 12 circumscribing the foam can be made of any suitable material having sufficient strength to compress and hold the foam member and to be handled during collecting and delivery of the specimen. Typical materials used for conventional straws, for example, paper tubes and polyethylene, polypropylene, polyester, vinyl or other plastic tubes, are suitable for the tube. Such straws also are economical and an appropriate diameter for, manufacturing of the collection device, handling and use. A circular cross section for the tube is preferred for convenience. However, other shaped cross sections, such as square or triangular tubes, also can be used.

The particular dimensions of the sample collecting device of the invention can vary depending upon the volume of specimen desired and the manner of handling the device for sample collection and delivery. For manual use, it is preferred that the tube length of the device be about 1.0 inch to about 5.0 inches long and that the mean cross sectional diameter of the tube be from about 0.12 to about 0.5 inch. More preferably, the tube is about 1.5 inches to about 3.5 inches long and has a mean cross sectional diameter from about 0.18 to about 0.38 inch.

A particularly useful collection device 10 has a circular hollow tube 12 three (3.0) inches long and 0.22 inch in diameter. An elongated foam member 15 is precut having a length of 3.5 inches and a square cross section 0.25 inch per side. The foam member 15 is compressed and inserted into the tube 12 so that 0.25 inch of foam protrudes on each end. This device can be used to collect a sample using either end, or to collect two samples using both ends. The tube provides a convenient handle to hold the device during use. Saliva can be collected by wicking the saliva into the foam member in as little as 15 seconds. The saliva can be delivered for diagnostic testing by dabbing the foam member onto a slide or membrane, or other device. Pressure also can be exerted on the tube to compress the foam and provide pressure to facilitate delivery of the sample.

Figure 3:
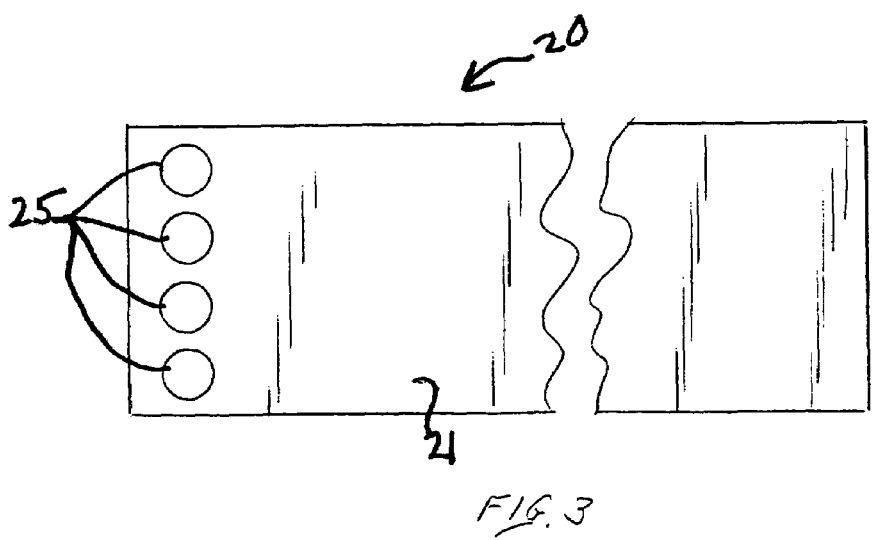
FIG. 3 is a plan view of a matrix collection device on which samples can be spotted for subsequent diagnostic testing.

The sample collection device of the present invention is particularly useful for collecting samples of saliva and spotting the samples on a matrix collection matrix device 20 (FIG. 3) for subsequent isolation of DNA for PCR. Conveniently, the collection matrix is provided in a card form having areas 25, e.g., circles, outlined for spotting the samples (see FIG. 3). After collecting the saliva, the foam is dabbed in the circle to spot a sample. After spotting the sample is dried. DNA is isolated from the spotted sample for analysis using a PCR technique (see, for example, Cheng et al., *Proc. Natl. Acad. Sci. USA*. 91: 5695–5699 or Wright et al., *J. Clin. Microbiol.* 32: 464–468). The collection matrix can be a conventional paper matrix or, preferably, a collection matrix sold under the brand name IsoCode™ by Schleicher & Schuell, Keene, N.H. 03431.

The collection device of the present invention can be used to provide samples for diagnostic analysis or identification of DNA, RNA, antibodies, drugs, and the like.

The invention has been described in detail with reference to preferred embodiments thereof. However, it will be appreciated that, upon consideration of the present specification and drawings, those skilled in the art may make modifications and improvements within the spirit and scope of this invention as defined by the claims.

I claim:

1. A specimen collecting device useful for collecting a fluid specimen for diagnostic testing consisting essentially of an elongated absorbent foam member having a longitudinal axis and an uncompressed cross sectional area, the elongated foam member being circumscribed by an elongated hollow, one-piece tubular member having a flexible side wall along a portion of the longitudinal axis, the hollow tubular member having a cross sectional area less than the uncompressed cross sectional area of the foam member so that the foam member is compressed by the hollow tubular member along the circumscribed portion, wherein the foam member consists of a material suitable for collecting a specimen of a patient fluid and the foam member remains circumscribed by the tubular member during collection of the specimen, and wherein pressure can be exerted on the side wall of the tubular member to compress the foam and deliver a sample of the fluid specimen.

2. The specimen collecting device of claim 1, wherein the hollow tubular member is made of paper or plastic.

3. The specimen collecting device of claim 1, wherein the foam member comprises a material selected from the group consisting of polyurethane foam, polyethylene foam, polyvinylchloride foam, ethylvinylacetate foam, polyethylene/ ethylvinylacetate foam, polyester foam and polyether foam.

4. The specimen collecting device of claim 1, wherein the foam member comprises a polyurethane foam.

5. The specimen collecting device of claim 1, wherein the foam member has a mean diameter in an uncompressed state, and wherein the foam member protrudes from an end of the tubular member a distance of about 25% to about 125% of said mean diameter of the uncompressed cross sectional area of the foam member.

6. The specimen collecting device of claim 1, wherein the hollow tubular member has a length of from about 1.0 inch to about 5.0 inches.

7. The specimen collecting device of claim 1, wherein the hollow tubular member has a mean diameter of from about 0.12 to about 0.5 inch.

8. The specimen collecting device of claim 1, wherein the hollow tubular member has a length of from about 1.5 inches to about 3.5 inches.

9. The specimen collecting device of claim 1, wherein the hollow tubular member has a mean diameter of from about 0.18 to about 0.38 inch.

10. A specimen collecting device useful for collecting a fluid specimen for diagnostic testing consisting essentially of an elongated absorbent foam member having a longitudinal axis and an uncompressed cross sectional area, the elongated foam member being circumscribed by an elongated hollow tubular member having a flexible side wall along a portion of the longitudinal axis, the hollow tubular member having a cross sectional area less than the uncompressed cross sectional area of the foam member so that the foam member is compressed by the hollow tubular member along the circumscribed portion, wherein the hollow tubular member has a mean diameter of from about 0.12 to about 0.5 inch, wherein the foam member consists of a material suitable for collecting a specimen of a patient fluid and the foam member remains circumscribed by the tubular member during collection of the specimen, and wherein pressure can be exerted on the side wall of the tubular member to compress the foam and deliver a sample of the specimen.

* * * * *